US012030825B2

(12) United States Patent
Gordon et al.

(10) Patent No.: US 12,030,825 B2
(45) Date of Patent: Jul. 9, 2024

(54) METHODS OF TRACING AND/OR SOURCING PLANT MATERIAL

(71) Applicant: ARIZONA BOARD OF REGENTS ON BEHALF OF ARIZONA STATE UNIVERSITY, Scottsdale, AZ (US)

(72) Inventors: Gwyneth Gordon, Tempe, AZ (US); Joseph Skulan, Lodi, WI (US); Odysseas Ladopoulos, Waunakee, WI (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 626 days.

(21) Appl. No.: 16/668,618

(22) Filed: Oct. 30, 2019

(65) Prior Publication Data

US 2020/0131097 A1    Apr. 30, 2020

Related U.S. Application Data

(60) Provisional application No. 62/752,720, filed on Oct. 30, 2018.

(51) Int. Cl.
*A01G 18/20*    (2018.01)
*A01G 7/00*    (2006.01)
(Continued)

(52) U.S. Cl.
CPC .............. *C05G 3/00* (2013.01); *A01G 7/00* (2013.01); *A01G 18/20* (2018.02); *A01G 22/00* (2018.02);
(Continued)

(58) Field of Classification Search
CPC ........ A01G 18/20; A01G 22/15; A01G 22/25; A01G 24/10; C05G 3/00
(Continued)

(56) References Cited

U.S. PATENT DOCUMENTS 3,854,240 A  *  12/1974  Oldham ................. C12P 1/00
                                                    435/89
4,431,738 A  *   2/1984  Maeda ................ C12N 5/0025
                                                   435/946

(Continued)

FOREIGN PATENT DOCUMENTS

CA       1281438      3/1991
WO     2011156583     12/2011

OTHER PUBLICATIONS

Flockhart et al., "Experimental evidence shows no fractionation of strontium isotopes (87Sr/86Sr) among soil, plants, and herbivores: implications for tracking wildlife and forensic science", Isotopes in Environmental and Health Studies, 51(3)372-381 (2015).

(Continued)

*Primary Examiner* — David J Parsley
(74) *Attorney, Agent, or Firm* — BOOTH UDALL FULLER, PLC

(57) ABSTRACT

Disclosed are methods of producing nutrient solutions having unique isotopic fingerprints; methods of producing traceable plants; and methods of identifying the source of a traceable plant that does not rely on expensive artificially separated isotopes. Plants grown with these nutrient solutions will have unique isotopic fingerprints that will be difficult or impossible to counterfeit.

9 Claims, 2 Drawing Sheets

(51) Int. Cl.

| | | |
|---|---|---|
| *A01G 22/00* | (2018.01) | |
| *A01G 22/15* | (2018.01) | |
| *A01G 22/25* | (2018.01) | |
| *A01G 22/35* | (2018.01) | |
| *A01G 24/10* | (2018.01) | |
| *A01G 31/00* | (2018.01) | |
| *C05G 1/00* | (2006.01) | |
| *C05G 3/00* | (2020.01) | |
| *C05G 5/23* | (2020.01) | |
| *G01N 33/24* | (2006.01) | |

(52) U.S. Cl.
CPC ............ *A01G 22/15* (2018.02); *A01G 22/25* (2018.02); *A01G 22/35* (2018.02); *A01G 24/10* (2018.02); *A01G 31/00* (2013.01); *C05G 1/00* (2013.01); *C05G 5/23* (2020.02); *G01N 33/24* (2013.01); *G01N 2033/245* (2013.01)

(58) Field of Classification Search
USPC ........................................ 47/1.01 R, 58.1 SC
See application file for complete search history.

(56) References Cited

U.S. PATENT DOCUMENTS

| | | |
|---|---|---|
| 4,866,270 A | 9/1989 | Hall |
| 5,012,052 A | 4/1991 | Hayes |
| 5,026,417 A * | 6/1991 | Kucey ................... A01N 63/36 435/933 |
| 5,324,658 A * | 6/1994 | Cox ....................... C12N 1/125 435/243 |
| 5,432,344 A | 7/1995 | Brand |
| 7,972,840 B2 * | 7/2011 | Hasegawa ............ C12M 29/04 47/60 |
| 9,261,519 B2 | 2/2016 | Anbar |
| 10,115,577 B1 | 10/2018 | Eiler |
| 10,302,565 B2 | 5/2019 | Steimle |
| 10,312,071 B2 | 6/2019 | Radke |
| 2002/0187552 A1* | 12/2002 | Cheung ................... C05F 3/00 71/21 |
| 2009/0114809 A1 | 5/2009 | Hotchkis |
| 2014/0273248 A1 | 9/2014 | Anbar |

OTHER PUBLICATIONS

Dolgin, "A Gold Rush for Cannibis," Nature, vol. 562, 327-330, 2018.

\* cited by examiner

METHODS OF TRACING AND/OR SOURCING PLANT MATERIAL

CROSS-REFERENCE TO RELATED APPLICATIONS

The present application claims priority to U.S. Provisional Patent Application No. 62/752,720 filed Oct. 30, 2018, which is hereby incorporated by reference in its entirety.

TECHNICAL FIELD

The disclosure relates to the use of natural isotopes to identify the source of plant material.

BACKGROUND

The growing movement toward legalization of *cannabis* has created a demand for reliable methods of tracing *cannabis* products to their producers. This demand is both the result of laws requiring legally produced *cannabis* to be distinguishable from illegally produced material and the result of *cannabis* producers themselves wanting reliable methods of distinguishing their own products from counterfeits. Some states, such as California, accomplish this by carefully tracking all legally-produced *cannabis*. However, as the *cannabis* industry grows and as legal *cannabis* use moves from dispensary-controlled medical applications to recreational use, systems that rely on chain of custody alone, such as California's, to identify the source of *cannabis* products will become difficult or impossible to maintain. An alternative approach, such as the proposal Colorado bill S029, is to require the addition of a chemical tracer to legally produced *cannabis*. While in principle, this alternative approach is simple and effective, adding chemical tracers to *cannabis* has met with widespread resistance by *cannabis* producers and users. Rational or not, the term "chemical additive" has powerfully and perhaps insurmountably negative connotations. Accordingly, there is a need for developing tracers than can shed the "chemical" label and is, preferably, a natural tracer.

SUMMARY

The disclosure is directed to methods of producing a nutrient solution with a unique radiogenic isotopic fingerprint and/or a unique mass-dependent isotopic fingerprint. The unique isotopic fingerprints are based on the isotopes of strontium (Sr), neodymium (Nd), calcium (Ca), magnesium (Mg), and/or potassium (K). In some aspects, the unique radiogenic isotopic fingerprint is the ratio of $^{87}Sr/^{86}Sr$, $^{87}Sr/^{84}Sr$, $^{87}Sr/^{88}Sr$, $^{143}Nd/^{144}Nd$, $^{143}Nd/^{142}Nd$, $^{143}Nd/^{145}Nd$, $^{143}Nd/^{146}Nd$, $^{143}Nd/^{148}Nd$, $^{143}Nd/^{150}Nd$. In some aspects, the unique mass-dependent isotopic fingerprint is the ratio of $^{87}Sr/^{86}Sr$, $^{42}Ca/^{44}Ca$, $^{24}Mg/^{26}Mg$ or $^{25}Mg/^{26}Mg$, and/or $^{39}K/^{41}K$.

The disclosure also relates to methods of producing traceable plants and method of identifying the source of a traceable plant using the nutrient solutions with a unique isotopic fingerprint.

In one aspect, the disclosure provides a method of producing a nutrient solution having a unique radiogenic isotopic fingerprint of strontium (Sr) and/or neodymium (Nd), wherein the unique radiogenic isotopic fingerprint of Sr is the ratio of $^{87}Sr/^{86}Sr$, $^{87}Sr/^{84}Sr$, or $^{87}Sr/^{88}Sr$ and the unique radiogenic isotopic fingerprint of Nd is the ratio of $^{143}Nd/^{144}Nd$, $^{143}Nd/^{142}Nd$, $^{143}Nd/^{145}Nd$, $^{143}Nd/^{146}Nd$, $^{143}Nd/^{148}Nd$, or $^{143}Nd/^{150}N$, the method comprising: providing a rock; leaching the rock with an organic acid or a mineral acid to create a leachate; drying the leachate; and removing the acid from the dried leachate.

In another aspect, the rock comprises a ratio of $^{87}Sr/^{86}Sr$ of greater than 1.0. In one implementation, the rock comprises a Sr concentration of greater than 20 ppm.

In another implementation, the rock comprises a ratio of $^{143}Nd/^{144}Nd$ of greater than 0.5130 or less than 0.5100. In one aspect, the rock comprises a Nd concentration of greater than 10 ppm.

In certain embodiments, the rock is granite. In one embodiment, the method further comprises crushing the rock into powder, wherein the step of leaching the rock with organic acid comprises mixing the rock powder with the organic acid. In some embodiments, the method further comprises analyzing the leachate for elemental composition.

In one aspect, the organic acid or mineral acid is selected from the group consisting of: acetic acid, oxalic acid, formic acid, ascorbic acid, nitric acid, and hydrochloric acid.

In another aspect, the step of removing the organic acid or mineral acid from the leachate comprises ashing the dried leachate at 400° C.

In some embodiments, the method further comprises removing iron from the leachate. In some embodiments, removing iron from the leachate comprises: dissolving the ashed leachate in nitric acid to produce a nitric acid solution; separating any solids from the nitric acid solution; and collecting the aqueous portion of the nitric acid solution.

In certain aspects, the method further comprises drying the aqueous portion of the nitric acid solution to produce a composition of nitrate salt.

In yet other embodiments, the method further comprises adding the dried leachate, ashed leachate, or the composition of nitrate salt to a nutrient solution to produce a nutrient solution with a unique radiogenic isotopic fingerprint of Sr and/or Nd.

In one embodiment, the method further comprises passing the leachate through a Sr-specific or Nd-specific cation exchange resin; and eluting the Sr-specific or Nd-specific cation exchange resin to extract a pure Sr salt or a pure Nd salt.

In some aspects, the method further comprises adding the pure Sr salt or pure Nd salt to a nutrient solution to produce a nutrient solution with a unique radiogenic isotopic fingerprint of Sr and/or Nd.

In yet other aspects, the disclosure provides a method of producing a nutrient solution having a unique mass-dependent isotopic fingerprint, the method comprising: providing a source of strontium (Sr), calcium (Ca), magnesium (Mg), potassium (K), boron (B), chlorine (Cl), copper (Cu), iron (Fe), manganese (Mn), molybdenum (Mo), and/or zinc (Zn); dissolving the source of Sr, Ca, Mg, K, B, Cl, Cu, Fe, Mn, Mo, and/or Zn; evaporating the dissolved source of Sr, Ca, Mg, K, B, Cl, Cu, Fe, Mn, Mo, and/or Zn at a temperature of no higher than room temperature until at least 95% of the dissolved material has been precipitated; separating the precipitate from the dissolved material; collecting the separated dissolved material; and adding the dissolved material to a nutrient solution to produce the nutrient solution with a unique mass-dependent isotopic fingerprint, wherein the unique mass-dependent isotopic fingerprint is the ratio of $^{88}Sr/^{86}Sr$, $^{42}Ca/^{44}Ca$ $^{24}Mg/^{26}Mg$ or $^{25}Mg/^{26}Mg$, $^{39}K/^{41}K$, $^{11}B/^{10}B$, $^{37}Cl/^{35}Cl$, $^{65}Cu/^{63}Cu$, $^{56}Fe/^{57}Fe$, $^{56}Fe/^{58}Fe$, $^{57}Fe/^{58}Fe$, $^{55}Mn/^{53}Mn$, $^{94}Mo/^{95}Mo$, $^{94}Mo/^{96}Mo$, $^{94}Mo/^{97}Mo$, $^{95}Mo/^{96}Mo$, $^{95}Mo/^{97}Mo$, $^{96}Mo/^{97}Mo$, $^{66}Zn/^{67}Zn$, $^{66}Zn/^{68}Zn$, and/or $^{67}Zn/^{68}Zn$.

In some aspects, the evaporating step is performed under vacuum. In other aspects, the source of Sr, Ca, Mg, K, B, Cl, Cu, Fe, Mn, Mo, and/or Zn is dissolved in water, acetone, or other solvent.

In one aspect, the dissolved source of Sr, Ca, Mg, K, B, Cl, Cu, Fe, Mn, Mo, and/or Zn is evaporated until 95-99% of the dissolved material has been precipitated. In another aspect, the step of collecting the dissolved material from the precipitate comprises filtering the precipitate from the dissolved material.

In certain embodiments, the source of Sr, Ca, Mg, K, B, Cl, Cu, Fe, Mn, Mo, and/or Zn is selected from the group consisting of: the nitrate, carbonates, phosphates, sulfates, and/or chlorides of Sr, Ca, Mg, K, B, Cl, Cu, Fe, Mn, Mo, and/or Zn.

In other embodiments, the disclosure provides a method of producing a traceable plant having a unique radiogenic isotopic fingerprint, the method comprising: adding to a growth medium a nutrient solution having a unique radiogenic isotopic fingerprint produced according to a method as disclosed herein and/or the nutrient solution with a unique mass-dependent isotopic fingerprint produced according to a method disclosed herein to produce an enriched growth medium; and growing a plant in the enriched growth medium.

In one embodiment, the growth medium is a hydroponic or aeroponic growth medium; and the nutrient solution with a unique radiogenic isotopic fingerprint and/or the nutrient solution with a unique mass-dependent isotopic fingerprint is added to the hydroponic or aeroponic growth medium prior to exposing the plant root to the hydroponic or aeroponic growth medium.

In some aspects, the concentration of the nutrient solution with a unique radiogenic isotopic fingerprint and/or mass-dependent isotopic fingerprint (i.e., tracer solution) is at least 20% in the growth medium. In other aspects, the concentration of the nutrient solution with a unique radiogenic isotopic fingerprint and/or mass-dependent isotopic fingerprint (i.e., tracer solution) is at least 5%, at least 10%, at least 15%, at least 20%, at least 25%, at least 30%, at least 35%, at least 40%, at least 45%, at least 50%, at least 60%, at least 70%, at least 80%, or at least 90% in the growth medium.

In yet other aspects, the concentration of the nutrient solution with a unique radiogenic isotopic fingerprint and/or mass-dependent isotopic fingerprint (i.e., tracer solution) is at least 0.01%, at least 0.05%, at least 0.1%, at least 0.2%, at least 0.3%, at least 0.4%, at least 0.5%, at least 0.6%, at least 0.7%, at least 0.8%, at least 0.9%, or at least 1.0% in the growth medium.

In certain aspects, the concentration of the nutrient solution with a unique radiogenic isotopic fingerprint and/or mass-dependent isotopic fingerprint (i.e., tracer solution) is between 0.01% and 10% in the growth medium, e.g., between 0.01% and 5%, between 0.01% and 1%, between 0.01% and 0.1%, between 0.1% and 10%, between 0.1% and 5%, between 0.1% and 1%, between 1% and 10%, or between 1% and 5% in the growth medium.

In some embodiments, the growth medium is soil, the plant is grown in a container, and the nutrient solution with a unique radiogenic isotopic fingerprint and/or mass-dependent isotopic fingerprint is evenly mixed with the soil in the container.

In certain embodiments, the method further comprises inducing drought stress and/or nutrient stress in the plant prior to growing the plant in the enriched growth medium to increase uptake of isotopes in the enriched growth medium by the plant.

In other embodiments, the disclosure provides a method of identifying the source of a traceable plant, the method comprising: providing a sample from a plant; removing extrinsic material from the sample; measuring the radiogenic isotopic fingerprint and/or the mass-dependent isotopic fingerprint of the sample; and if the radiogenic isotopic fingerprint and/or the mass-dependent isotopic fingerprint of the sample matches the radiogenic isotopic fingerprint and/or the mass-dependent isotopic fingerprint of an enriched growth medium, identifying the user of the enriched growth medium as the source of the plant.

In certain aspects, the step of removing extrinsic material from the plant sample comprises rinsing the sample in distilled water.

In other aspects, measuring the radiogenic isotopic fingerprint and/or the mass-dependent isotopic fingerprint of the plant comprises determining, in the sample, the ratio of at least one of: $^{87}Sr/^{86}Sr$, $^{87}Sr/^{84}Sr$, $^{87}Sr/^{88}Sr$, $^{143}Nd/^{144}Nd$, $^{143}Nd/^{142}Nd$, $^{143}Nd/^{145}Nd$, $^{143}Nd/^{146}Nd$, $^{143}Nd/^{148}Nd$, $^{143}Nd/^{150}Nd$, $^{42}Ca/^{44}Ca$, $^{24}Mg/^{26}Mg$, $^{25}Mg/^{26}Mg$, $^{39}K/^{41}K$, $^{11}B/^{10}$, $^{37}Cl/^{35}Cl$, $^{65}Cu/^{63}Cu$, $^{56}Fe/^{57}Fe$, $^{56}Fe/^{58}Fe$, $^{57}Fe/^{58}Fe$, $^{55}Mn/^{53}Mn$, $^{94}Mo/^{95}Mo$, $^{94}Mo/^{96}Mo$, $^{94}Mo/^{97}Mo$, $^{95}Mo/^{96}Mo$, $^{95}Mo/^{97}Mo$, $^{96}Mo/^{97}Mo$, $^{66}Zn/^{67}Zn$, $^{66}Zn/^{68}Zn$, $^{67}Zn/^{68}Zn$.

In some embodiments, the radiogenic isotopic fingerprint and/or the mass-dependent isotopic fingerprint of the sample is measured with isotope-ratio mass spectrometry (IRMS).

In one aspect, the plant is *cannabis*.

In certain aspects, the disclosure provides a composition comprising: an element selected from the group consisting of strontium (Sr), neodymium (Nd), calcium (Ca), magnesium (Mg), potassium (K), boron (B), chlorine (Cl), copper (Cu), iron (Fe), manganese (Mn), molybdenum (Mo), zinc (Zn), and combinations thereof; wherein stable isotopes of the element are present in a mixture that provides an isotopic fingerprint for tracing the source of a biological material into which the composition has been incorporated.

In one aspect, the mixture of stable isotopes is selected from the group consisting of $^{87}Sr/^{86}Sr$, $^{87}Sr/^{84}Sr$, $^{87}Sr/^{88}Sr$, $^{143}Nd/^{144}Nd$, $^{143}Nd/^{142}Nd$, $^{143}Nd/^{145}Nd$, $^{143}Nd/^{146}Nd$, $^{143}Nd/^{148}Nd$, $^{143}Nd/^{150}Nd$, $^{42}Ca/^{44}Ca$, $^{24}Mg/^{26}Mg$, $^{25}Mg/^{26}Mg$, $^{39}K/^{41}K$, $^{11}B/^{10}$, $^{37}Cl/^{35}Cl$, $^{65}Cu/^{63}Cu$, $^{56}Fe/^{57}Fe$, $^{56}Fe/^{58}Fe$, $^{57}Fe/^{58}Fe$, $^{55}Mn/^{53}Mn$, $^{94}Mo/^{95}Mo$, $^{94}Mo/^{96}Mo$, $^{94}Mo/^{97}Mo$, $^{95}Mo/^{96}Mo$, $^{95}Mo/^{97}Mo$, $^{96}Mo/^{97}Mo$, $^{66}Zn/^{67}Zn$, $^{66}Zn/^{68}Zn$, $^{67}Zn/^{68}Zn$, and combinations thereof.

In certain aspects, the composition further comprises nitrogen (N), phosphorus (P), and potassium (K) in an amount sufficient to support the growth of a plant. In one aspect, the nitrogen (N) is present as a nitrate salt and/or the phosphorus (P) is present as a phosphate salt. In another aspect, the composition is a hydroponic or aeroponic solution.

In some embodiments, the concentration of the element is at least 10 ppm. In one embodiment, the composition comprises strontium (Sr) in a ratio of $^{87}Sr/^{86}Sr$ of greater than 1.0. In another embodiment, the composition comprises neodymium (Nd) in a ratio of $^{413}Nd/^{144}Nd$ of greater than 0.5130 or less than 0.5100.

In certain implementations, the composition is a formulated as an aqueous solution or a seed treatment. In one implementation, the composition further comprises an agriculturally acceptable carrier.

In some embodiments, the biological material is a high value crop selected from the group consisting of *cannabis, ginseng*, a gourmet mushroom, a gourmet garlic, and a rare herb. In one embodiment, the biological material is a cell culture. In certain aspects, the cell culture comprises rhizobacteria or mycorrhizal fungi. In one embodiment, the rhizobacteria or mycorrhizal fungi are used as a vector or carrier to transfer the mixture of stable isotopes from the composition to a plant or crop.

DETAILED DESCRIPTION

Figure 1:
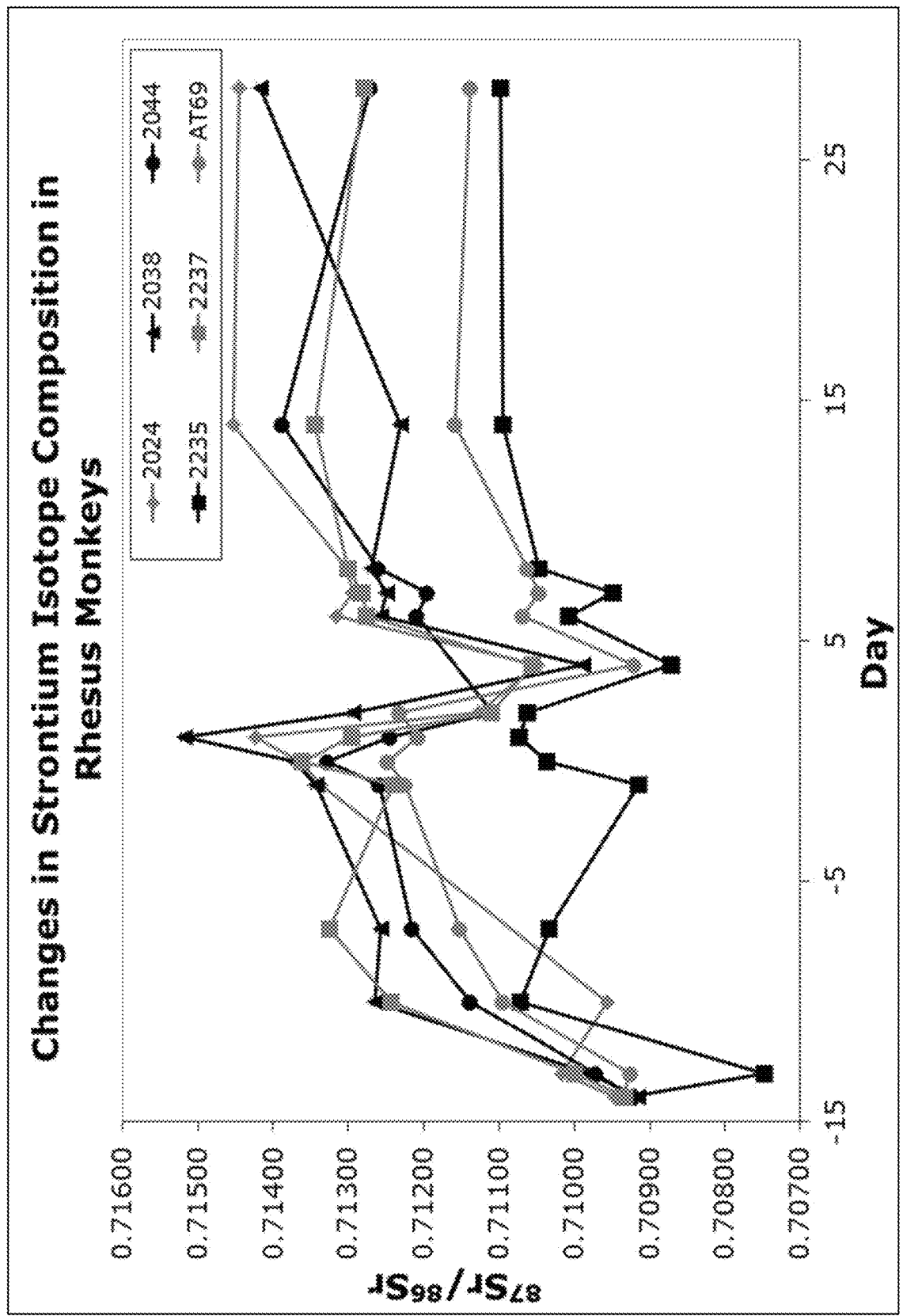
FIG. 1 depicts changes in strontium isotope composition in rhesus monkeys fed a diet supplemented with strontium extracted from ancient granite during a two week acclimation period followed by experimentally induced bone loss.

Detailed aspects and applications of the disclosure are described below in the following drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that embodiments of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

As used herein, the term "about" refers to a deviation no more than 0.5% of the given value, for example a deviation of 0.1% of the given value.

As used herein, the term "growth medium" refers to the soil in which a plant is grown or to an aeroponic or hydroponic nutrient solution.

As used herein, the term "sample" refers to any portion of a plant, including but not limited to, the plant's leaf, flower, bud, stalk, root, or seed. The term also includes dried portions of the plant.

As used herein, the term "rock" refers to a substance that is a solid aggregate of one or more minerals or mineraloids. For example, the term encompasses igneous rock, such as granite, as well as sedimentary rock and metaphoric rock.

As used herein, the term "room temperature" refers to a temperature range of between 20° C. and 25° C., between 20° C. and 22° C., between 18° C. and 22° C., about 20° C., or about 22° C. Accordingly, a temperature that is no higher than room temperature refers to a temperature of less than 25° C.

The disclosure relates to the use of isotopic labeling as a possible alternative to chemical tracers in tracing the origins of plants. Isotopic labeling does not require the use of artificially separated isotopes. By carefully selecting source materials, and by simple modifications in production techniques, it is possible to create plant fertilizers with anomalous isotope compositions that will impart a unique isotopic fingerprint on plants grown with these plant fertilizers. The unique isotopic fingerprint includes both radiogenic and mass-dependent isotopic labels.

The stable isotopes most commonly used for labeling organic material are those of carbon, nitrogen, and oxygen. But, for several reasons these isotopes are poorly suited to labeling plants, especially plants for human use such a *cannabis*. First, carbon, nitrogen, and oxygen are major components of plant tissues. Altering the isotopic composition of these elements would require large amounts of expensive purified isotope tracers. Second, as much of the oxygen and almost all of the carbon in plant tissues is derived from $CO_2$, administering carbon or oxygen isotope tracers to plants would require controlling the isotopic composition of the air around the plants, which would be difficult, inefficient, and expensive. Third, although artificially separated isotopic tracers administered to growing plants would not alter the plants' chemical composition, "artificially separated isotopic tracers" may still carry enough of a negative connotation to create resistance to their widespread acceptance. However, natural isotopes of strontium (Sr), neodymium (Nd), calcium (Ca), magnesium (Mg), or potassium (K) are suitable for labeling plants without the need for expensive purified isotope tracers or artificially separated isotopic tracers. Instead, the disclosure provides methods of producing isotopically labeled compositions.

For compliance with regulations on tracing the source of *cannabis*, isotopic labels are included in Colorado S029. With isotopic labeling, no new chemical is added to *cannabis*, as all of the elements listed naturally occur in all plant tissues. Rather, the stable (non-radioactive) isotopic composition of chemicals already present in *cannabis* is altered in a characteristic way that can be detected by mass spectrographic analysis of *cannabis* products. Accordingly, the nutrient solutions with a unique isotopic fingerprint, such as the isotopic compositions produced according to the methods described herein, are particularly useful for tracing the source of *cannabis* and products made from *cannabis*.

In other aspects, the nutrient solutions with a unique isotopic fingerprint, such as the isotopic compositions produced according to the methods described herein, are useful for tracing the source of high value crops. High value crops include, but are not limited to, *cannabis, ginseng,* gourmet mushrooms (e.g., oyster mushrooms and shiake mushrooms), gourmet garlic (also known as hardneck garlic (e.g., Rocambole, Purplestripe and Porcelain), and rare herbs (e.g., saffron).

In one aspect, the disclosure relates to methods of producing a nutrient solution with a unique radiogenic isotopic fingerprint, for example, one based on Sr and/or Nd. In accordance to some certain embodiments, the unique radiogenic isotopic fingerprint is the ratio of $^{87}Sr/^{86}Sr$ and/or the ratio of $^{143}Nd/^{144}Nd$.

Natural Sr is a mix of four stable (non-radioactive) isotopes, with masses 84, 86, 87, and 88, with relative abundances of about 0.56%, 9.86%, 7.0%, and 82.58%, respectively. The amount of $^{84}Sr$, $^{86}Sr$, and $^{88}Sr$ do not change over time, but the amount of $^{87}Sr$ increases over time due to the decay of rubidium-87($^{87}Rb$) to $^{87}Sr$, with a half-life of about 49 billion years. In very old rocks, and/or rocks with a high Rb/Sr ratio, measurement of the abundance of $^{87}Sr$ relative to other Sr isotopes (for example, expressed as the ratio $^{87}Sr/^{86}Sr$) can be used as the basis of a radiometric dating technique. Because rocks tend to develop characteristic ratio of $^{87}Sr$, measurement of the ratio the ratio $^{87}Sr/^{86}Sr$ has also been used to trace the source of minerals in groundwater, in animal tissues, and in foodstuffs (see, for example, Marchionni et al., *J. Agric. Food Chem.*, 2013, 61(28):6822-6831). $^{87}Sr/^{86}Sr$ has also be used to determine water source and as a tracer in studies of Ca metabolism. The ratios of $^{87}Sr$ in relation to any of the two other natural Sr isotopes (for example, $^{87}Sr/^{84}Sr$ and $^{87}Sr/^{88}Sr$) can also be the basis of a unique isotopic fingerprint.

Sr is chemically similar to Ca, and all natural sources of Ca, including plant and animal tissues, contain some Sr. The concentration of Sr relative to Ca is a few hundred to a few thousand parts per million (ppm). Plant and animal tissues acquire the same $^{87}Sr/^{86}Sr$ as that of their nutrient source, which for plants is soil and groundwater. The $^{87}Sr/^{86}Sr$ of 95 municipal water sources in the US ranges from 0.7037 to 0.7320 (Chesson et al., *Ecosphere*, 2012, 3(7):67). This range would also encompass that of the vast majority of plants grown in the US. Ancient rocks, however, can have much higher $^{87}Sr/^{86}Sr$. Ancient granites in northern Michigan, for example, can have $^{87}Sr/^{86}Sr$ of 1.0-1.2.

Nd isotopes can be used in the same way as Sr isotopes. Nd has seven natural isotopes (masses and abundances: 142, 27.2%; 143, 12.2%; 144, 23.8%; 145, 8.3%; 146, 17.2%; 148, 5.8%; 150, 5.6%). $^{143}Nd$ is the decay produce of samarium-147 ($^{147}Sm$), with a half-life of about 100 billion years. Variations in $^{143}Nd/^{144}Nd$ are an order of magnitude smaller than those of $^{87}Sr/^{86}Sr$, but the ratio of $^{143}Nd/144Nd$, as well as of $^{143}Nd/^{142}Nd$, $^{143}Nd/^{145}Nd$, $^{143}Nd/^{146}Nd$, $^{143}Nd/^{148}Nd$, and $^{143}Nd/^{150}Nd$, are used in similar ways, namely that these ratios can be the basis of a unique isotopic fingerprint.

Both Sr and Nd can be extracted from rocks by acid leaching. The methods described herein will not produce toxic residue. As such, the acids used in the methods will not include acids that are toxic or produce a toxic byproduct, such as hydrofluoric acid or perchloric acid. In certain implementations, methods will only minimally alter the source rock, which allows the rock to be used for other purposes, such as in landscaping, or as a soil amendment. Surprisingly, aggressive extraction methods that extract all Sr or Nd from the source rock are not necessary for an isotopic composition to have a unique radiogenic fingerprint for use in nutrient solution to produce traceable plants.

In accordance with certain embodiments, the method of producing a nutrient solution with a unique radiogenic isotopic fingerprint of Sr and/or Nd comprise providing a rock source, such as an ancient granite, with a sufficiently high ratio of $^{87}Sr/^{86}Sr$ and/or $^{143}Nd/^{144}Nd$; leaching the rock with organic and/or mineral acids to create a leachate; drying the leachate; and removing the organic acid or mineral acids from the dried leachate. In certain implementations, the organic acid or mineral acids used to create the leachate is acetic acid, oxalic acid, formic acid, ascorbic acid, nitric acid, or hydrochloric acid.

In some aspects, a sufficiently high ratio of $^{87}Sr/^{86}Sr$ in the rock source is a ratio of greater than about 1.0 while a sufficiently high ratio of $^{143}Nd/^{144}Nd$ is greater than about 0.5130. However, in some aspects, the ratio of $^{143}Nd/^{144}Nd$ in the rock source is less than about 0.5100. Preferably, the rock source comprises both a sufficiently high ratio of $^{87}Sr/^{86}Sr$ and/or $^{143}Nd/^{144}Nd$ along with a high concentration of Sr or Nd, respectively. In some aspects, the implementations, the rock source comprises a ratio of $^{87}Sr/^{86}Sr$ of greater than about 1.0 and a Sr concentration of greater than about 20 ppm, such as ancient granite. In some aspects, the rock comprises a ratio of $^{143}Nd/^{144}Nd$ of greater than about 0.5130 or less than about 0.5100 and a Nd concentration of greater than 10 ppm. In certain implementations, the rock source is crushed into powder, and the powder is mixed with the organic acid or mineral acid to create the leachate. In certain embodiments, the step of removing the organic acids from the leachate comprises ashing the dried leachate at 400° C. or higher.

In accordance with some implementations, the method further comprises analyzing the leachate for elemental composition. If the elemental composition of the leachate excess lead or uranium (as determined by relevant governmental or non-governmental regulations), the excess lead or uranium will be removed according to methods known in the art. Iron from the leachate should also be removed. Methods for iron removal could take advantage of the low solubility of iron in nitric acid. Thus, in some implementations, the method further comprises dissolving the ashed leachate in nitric acid to produce a nitric acid solution; separating any solids from the nitric acid solution; and collecting the aqueous portion of the nitric acid solution. In accordance with certain implementations, the aqueous portion of the nitric acid solution is dried to produce a composition of nitrate salt. The nutrient solution with a unique radiogenic isotopic fingerprint of Sr and/or Nd is produced by adding the dried leachate, ashed leachate, or the composition of nitrate salt to a conventional nutrient solution.

In other implementations, the nutrient solution with a unique radiogenic isotopic fingerprint of Sr and/or Nd is produced by adding to a conventional nutrient solution pure Sr nitrate or pure Nd nitrate produced from dissolving the ashed leachate in nitric acid and passing the solution through a Sr-specific or Nd-specific cation exchange resin to extract the pure Sr nitrate or pure Nd nitrate.

In one aspect, the disclosure relates to methods of producing a nutrient solution with a unique mass-dependent isotopic fingerprint. The mass-dependent isotopes that provide a unique isotopic fingerprint are those of Sr, Ca, Mg, or K. The method of producing a nutrient solution with a unique mass-dependent isotopic fingerprint is based on the principle that materials that crystallize from solution generally have a different isotopic composition from the material remaining in solution. Typically, lower mass isotopes crystallize at a slightly higher rate than higher mass (heavier) isotopes, with a constant offset in isotope composition between the solution and the newly precipitated crystal. As a result, in a system where no new material is added to solution, the residue of material remaining in solution becomes highly enriched in heavy isotopes as the fraction of initially dissolved material that precipitates approaches 100% (also known as "Rayleigh distillation"). For example, the $^{42}Ca/^{44}Ca$ ratio of Ca mineral precipitated from solution typically is 0.3-0.6‰ (+0.03-0.06%) lower than that of the solution. Assuming that this difference is 0.5‰, the last 5% of Ca remaining in solution will have a $^{42}Ca/^{44}Ca$ ratio 1.5‰ higher than the initial value. Ca nitrate nutrient solution with a $^{42}Ca/^{44}Ca$ ratio 1.5-2‰ higher than average would be isotopically distinct enough to qualify as isotopically labeled.

In accordance with certain embodiments, the method comprises providing a source of Sr, Ca, Mg, and/or K and dissolving the source of Sr, Ca, Mg, and/or K. The source of Sr, Ca, Mg, and/or K may be the nitrate, carbonates, phosphates, sulfates, and/or chlorides of Sr, Ca, Mg, and K. In certain implementations, the source of Sr, Ca, Mg, and/or K is an ordinary fertilizer, for example calcium nitrate. As such, the source of Sr, Ca, Mg, and/or K is dissolved in water, acetone, or another suitable solvent. The method further comprises evaporating the dissolved source of Sr, Ca, Mg, and/or K at temperatures no higher than room temperature until at least 95% (preferably between 95-99%) of the dissolved material has been precipitated and collecting the remaining dissolved material. Thus, the method may comprise separating the precipitate from the dissolved material (for example by filtration) and collecting the separated dissolved material. The collected separated dissolved material is then added to a conventional nutrient solution or ordinary fertilizer to produce the nutrient solution with a unique mass-dependent isotopic fingerprint. The duration of evaporation step can be reduced by performing it under vacuum. In some aspects, the unique mass-dependent isotopic fingerprint is the ratio of $^{88}Sr/^{86}Sr$, $^{42}Ca/^{44}Ca$, $^{24}Mg/^{26}Mg$, $^{25}Mg/^{26}Mg$, and/or $^{39}K/^{41}K$.

Additional mass-dependent isotopes that may be used to provide a unique isotopic fingerprint include naturally occurring isotopes of the plant micronutrients boron (B), chlorine (Cl), copper (Cu), iron (Fe), manganese (Mn), molybdenum (Mo), and zinc (Zn). These mass dependent isotopes are prepared according to the techniques disclosed herein. Unique mass-dependent isotopic fingerprints generated with these isotopes include the following ratios and combinations thereof: $^{11}B/^{10}B$, $^{37}Cl/^{35}Cl$, $^{65}Cu/^{63}Cu$, $^{56}Fe/^{57}Fe$, $^{56}Fe/^{58}Fe$, $^{57}Fe/^{58}Fe$, $^{55}Mn/^{53}Mn$, $^{94}Mo/^{95}Mo$, $^{94}Mo/^{96}Mo$, $^{94}Mo/^{97}Mo$, $^{95}Mo/^{96}Mo$, $^{95}Mo/^{97}Mo$, $^{96}Mo/^{97}Mo$, $^{66}Zn/^{67}Zn$, $^{66}Zn/^{68}Zn$, and $^{67}Zn/^{68}Zn$.

The disclosure also related to methods of producing traceable plants, wherein the plants are grown using the nutrient solutions with a unique isotopic fingerprint produced according to the methods described herein. For example, the method comprises adding the nutrient solution with a unique radiogenic isotopic fingerprint of Sr and/or Nd and/or the nutrient solution with a unique mass-dependent isotopic fingerprint to a growth medium to produce an enriched growth medium. The plant grown in the enriched growth medium would possess the unique isotopic fingerprint of the nutrient solution. Thus, by matching the isotopic fingerprint of the plant to that of an enriched growth medium, the source of the plant can be traced.

In some aspects, where the growth medium is a hydroponic or aeroponic growth medium, the nutrient solution with a unique isotopic fingerprint is added to the growth medium prior to exposing the plant root to the growth medium. Where the nutrient solution with a unique isotopic fingerprint is a nutrient solution with a unique radiogenic isotopic fingerprint made without using a Sr-specific or Nd-specific resin, the volume of the nutrient solution with a unique radiogenic isotopic fingerprint is at least 20% of the volume of the growth medium. Where the nutrient solution with a unique isotopic fingerprint is a nutrient solution with a unique radiogenic isotopic fingerprint made using a Sr-specific or Nd-specific resin, the volume of the nutrient solution with a unique radiogenic isotopic fingerprint can be less than 20% of the volume of the growth medium. In other aspects, where the growth medium is soil and the plant is grown in a container, the nutrient solution with a unique isotopic fingerprint is evenly mixed with the soil in the container prior to sprouting or growing the plant.

In certain aspects, the method further comprises inducing drought stress and/or nutrient stress in the plant prior to growing the plant in the enriched growth medium to increase uptake of isotopes in the enriched growth medium by the plant.

Nutrient stress is induced by contacting the plant with a growth medium comprising an amount of at least one nutrient that is less than the amount of that nutrient necessary for the optimal growth and development of the plant in the growth medium. The nutrient may be any one of nitrogen, phosphorus, potassium, calcium, magnesium, iron, manganese, zinc, boron, copper, molybdenum, or any combination thereof. In one embodiment, the nutrient is calcium. In another embodiment, the nutrient is potassium.

Drought stress is induced by contacting the plant with an amount of water less than the amount of water necessary for the optimal growth and development of the plant. Drought stress may be enhanced by exposing the plant to an elevated light intensity (e.g., at greater than 750 W/m², 800 W/m², 850 W/m², 900 W/m², 950 W/m², 1000 W/m², 1050 W/m², or 1100 W/m²) and/or increased temperature (e.g., a temperature greater than 25° C., 30° C., 35° C., or 40° C.).

In some embodiments, the nutrient solution applied to the plant after the stress compensates for the induced stress. If drought stress/heat stress was induced, the nutrient solution will be applied with frequent watering of the plant. If nutrient stress was induced, the nutrient solution will contain increased concentrations of the macronutrients and/or micronutrients that were lacking during the nutrient deprivation.

In certain implementations, the isotopes disclosed herein are applied as nutrient solutions to plants grown in a greenhouse. In other implementations, the isotopes disclosed herein are applied as nutrient solutions to plants grown in a greenhouse in a hydroponic or aeroponic system. In yet other implementations, the isotopes disclosed herein are applied as nutrient solutions to plants grown in a field.

In accordance with certain implementations, the method of identifying the source of a traceable plant comprises providing a sample from a plant; removing extrinsic material from the sample; measuring the radiogenic isotopic fingerprint and/or the mass-dependent isotopic fingerprint of the sample; and identifying the user of the enriched growth medium as the source of the plant if the radiogenic isotopic fingerprint and/or the mass-dependent isotopic fingerprint of the sample matches the radiogenic isotopic fingerprint and/or the mass-dependent isotopic fingerprint of an enriched growth medium. In some embodiments, any extrinsic material is removed from the plant sample by rinsing the sample with distilled water. In preferred implementations, the ratio of at least one of $^{87}Sr/^{86}Sr$, $^{87}Sr/^{84}Sr$, $^{87}Sr/^{g}Sr$, $^{88}Sr/^{86}Sr$, $^{143}Nd/^{144}Nd$, $^{143}Nd/^{142}Nd$, $^{143}Nd/^{145}Nd$, $^{143}Nd/^{146}Nd$, $^{143}Nd/^{148}Nd$, $^{143}Nd/^{150}Nd$, $^{42}Ca/^{44}Ca$, $^{24}Mg/^{26}Mg$, $^{25}Mg/^{26}Mg$, and $^{39}K/^{41}K$ in the sample is measured to determine the radiogenic isotopic fingerprint and/or the mass-dependent isotopic fingerprint of the sample. In other aspects, the ratio of at least one of $^{87}Sr/^{86}Sr$, $^{87}Sr/^{84}Sr$, $^{87}Sr/^{88}Sr$, $^{143}Nd/^{144}Nd$, $^{143}Nd/^{142}Nd$, $^{143}Nd/^{145}Nd$, $^{143}Nd/^{146}Nd$, $^{143}Nd/^{148}Nd$, $^{143}Nd/^{150}Nd$, $^{42}Ca/^{44}Ca$, $^{24}Mg/^{26}Mg$, $^{25}Mg/^{26}Mg$, $^{39}K/^{41}K$, $^{11}B/^{10}B$, $^{37}Cl/^{35}Cl$, $^{65}Cu/^{63}Cu$, $^{56}Fe/^{57}Fe$, $^{56}Fe/^{58}Fe$, $^{57}Fe/^{58}Fe$, $^{55}Mn/^{53}Mn$, $^{94}Mo/^{95}Mo$, $^{94}Mo/^{96}Mo$, $^{94}Mo/^{97}Mo$, $^{95}Mo/^{96}Mo$, $^{95}Mo/^{97}Mo$, $^{96}Mo/^{97}Mo$, $^{66}Zn/^{67}Zn$, $^{66}Zn/^{68}Zn$, and $^{67}Zn/^{68}Zn$ in the sample is measured to determine the radiogenic isotopic fingerprint and/or the mass-dependent isotopic fingerprint of the sample. In some aspects, the sample is from a traceable plant produced according to the methods described herein.

In some embodiments, the radiogenic isotopic fingerprint and/or the mass-dependent isotopic fingerprint of the sample is measured with isotope-ratio mass spectrometry (IRMS). IRMS is a well-known analytical technique which is a specific type of mass spectrometry. In IRMS, mass spectrometric methods are used to measure the relative abundance of isotopes in a given sample. It has been applied most commonly in chemistry, earth sciences and environmental sciences. In these fields it is used for the analysis of stable isotopes which is normally concerned with measuring isotopic variations arising from mass-dependent isotopic fractionation in natural systems. As used herein the term Isotope Ratio Mass Spectrometry (IRMS) encompasses both GC-IRMS (Gas Chromatography IRMS) and EA-IRMS (elemental analyzer IRMS). The IRMS technique allows the precise measurement of mixtures of naturally occurring isotopes. The IRMS technique and spectrometers for use therein have been described in, for example, U.S. Pat. Nos. 4,866,270, 5,012,052, 5,432,344 and US20090114809, U.S. Ser. No. 10/115,577, and U.S. Ser. No. 10/312,071, all of which are incorporated herein by reference.

In certain implementations, the disclosure relates to a composition or tracer solution comprising one or more isotopes disclosed herein. In one aspect, the tracer solution is added to a nutrient solution to be applied to a plant. In another aspect, the tracer solution is added to water used to irrigate the plant.

In certain aspects, the tracer solution is used to label a small number of plants that are processed and mixed with a bulk of plants to distribute the isotopically labelled plants throughout the final batch of processed plant material.

In some embodiments, the composition or tracer solution further comprises an agriculturally acceptable carrier. As used herein, the term "agriculturally acceptable" carrier refers to an acceptable carrier that may be applied to a crop without inducing toxicity to the crop. Examples of agriculturally acceptable carriers include, but are not limited to, a dispersant, a surfactant, an additive, a thickener, an anticaking agent, a composting formulation, a granular application, diatomaceous earth, an oil, a coloring agent, a stabilizer, a preservative, and a polymer.

In certain aspects, the disclosure relates to a hydroponic or aeroponic solution comprising one or more isotopes disclosed herein. In one implementation, the hydroponic or aeroponic solution further comprises one or more of the following compounds: $Ca(NO_3)_2 \cdot 3H_2O$, $KNO_3$, Fe-DTPA, $KH_2PO_4$, $MgSO_4 \cdot 7H_2O$, $K_2SO_4$, $MnSO_4 \cdot H_2O$, $H_3BO_3$, $Na_2MoO_4 \cdot 2H_2O$, $ZnSO_4 \cdot 7H_2O$, $CuSO_4 \cdot 5H_2O$. In one aspect, the hydroponic or aeroponic solution comprises calcium nitrate and one or more of the isotopes disclosed herein. In another aspect, the hydroponic or aeroponic solution comprises potassium nitrate and one or more of the isotopes disclosed herein.

In certain implementations, the composition or tracer solution comprises an element selected from the group consisting of strontium (Sr), neodymium (Nd), calcium (Ca), magnesium (Mg), potassium (K), boron (B), chlorine (Cl), copper (Cu), iron (Fe), manganese (Mn), molybdenum (Mo), zinc (Zn), and combinations thereof; wherein stable isotopes of the element are present in a mixture that provides an isotopic fingerprint for tracing the source of a biological material into which the composition has been incorporated.

In one aspect, the mixture of stable isotopes is selected from the group consisting of $^{87}Sr/^{86}Sr$, $^{87}Sr/^{4}Sr$, $^{7}Sr/^{88}Sr$, $^{143}Nd/^{144}Nd$, $^{143}Nd/^{142}Nd$, $^{143}Nd/^{145}Nd$, $^{143}Nd/^{146}Nd$, $^{143}Nd/^{148}Nd$, $^{143}Nd/^{150}Nd$, $^{42}Ca/^{44}Ca$, $^{24}Mg/^{26}Mg$, $^{25}Mg/^{26}Mg$, $^{39}K/^{41}K$, $^{11}B/^{10}B$, $^{37}Cl/^{35}Cl$, $^{65}Cu/^{63}Cu$, $^{56}Fe/^{57}Fe$, $^{56}Fe/^{58}Fe$, $^{57}Fe/^{58}Fe$, $^{55}Mn/^{53}Mn$, $^{94}Mo/^{95}Mo$, $^{94}Mo/^{96}Mo$, $^{94}Mo/^{97}Mo$, $^{95}Mo/^{96}Mo$, $^{95}Mo/^{97}Mo$, $^{96}Mo/^{97}Mo$, $^{66}Zn/^{67}Zn$, $^{66}Zn/^{68}Zn$, $^{67}Zn/^{68}Zn$, and combinations thereof. In one aspect, the isotopic fingerprint from the mixture of any set of these isotopes (e.g., $^{42}Ca/^{44}Ca$) is based on a ratio that is greater than 0.01, 0.05, 0.1, 0.2, 0.3, 0.4, 0.5, 0.6, 0.7, 0.8, 0.9, 1.0, 2.0, 3.0, 4.0, or 5.0. In another aspect, the isotopic fingerprint from the mixture of any set of these isotopes (e.g., $^{42}Ca/^{44}Ca$) is based on a ratio that is less than 0.01, 0.05, 0.1, 0.2, 0.3, 0.4, 0.5, 0.6, 0.7, 0.8, 0.9, 1.0, 2.0, 3.0, 4.0, or 5.0. In yet other aspects, the ratio characteristic of the isotopic fingerprint is between 0.01 and 5.0 (i.e., including any range between 0.01 and 5.0 such as between 0.01 and 1.0, between 0.01 and 0.5, between 0.01 and 0.1, between 0.1 and 5.0, between 0.1 and 1.0, between 0.5 and 5.0, between 0.5 and 2.0, etc.).

In certain implementations, the concentration of the element in the composition or tracer solution is at least 10 ppm, at least 20 ppm, at least 30 ppm, at least 40 ppm, at least 50 ppm, at least 60 ppm, at least 70 ppm, at least 80 ppm, at least 90 ppm, at least 100 ppm, at least 200 ppm, at least 300 ppm, at least 400 ppm, at least 500 ppm, at least 600 ppm, at least 700 ppm, at least 800 ppm, at least 900 ppm, or at least 1000 ppm. In one aspect, the concentration of the element is at least 10 ppm. In another aspect, the concentration of the element is at least 100 ppm. In yet another aspect, the concentration of the element is at least 1000 ppm.

Illustrative, Non-Limiting Example in Accordance with Certain Embodiments

The disclosure is further illustrated by the following examples that should not be construed as limiting. The contents of all references, patents, and published patent applications cited throughout this application are incorporated herein by reference in their entirety for all purposes.

Acid Leaching to Extract Sr and/or Nd

The process will include some or all of the following steps:
1. Identifying a granite source with $^{87}Sr/^{86}Sr$ of >1.0 and a Sr concentration of >20 ppm.
2. Crushing granite to a powder.
3. Leaching crushed granite with organic acids to remove at least 10 grams/ton (50% at 20 ppm) of the Sr, along with other metals.
4. Analyzing leachate for elemental composition, and removing excess lead and uranium, if present.
5. Drying leachate.
6. Ashing leachate at 400° C. for several hours to burn off organic acids and convert metals to oxides.
7. Redissolving the ashed leachate in nitric acid to convert most metals to nitrates. This step will also remove excess iron, which dissolves poorly in nitric acid.
7. Drying nitric acid solution. The result has a high $^{87}Sr/^{86}Sr$ that can be added to calcium nitrate used in hydroponic solutions used to grow *cannabis*.
8. Rinsing *cannabis* products in distilled water to remove an extrinsic material (including counterfeit isotopic tracers added post-production).
9. Measuring $^{87}Sr/^{86}Sr$ of *cannabis* product.

If desirable, pure Sr can be prepared by passing the solution in step 6 over a Sr-specific cation exchange resin.

The amount of granite-derived Sr needed to sufficiently alter $^{87}Sr/^{86}Sr$ of the nutrient solution (e.g., raise $^{87}Sr/^{86}Sr$ from about 0.71 to >0.76) will be about 20% of the amount already present in the solution to which it is added (e.g., about 20 grams per ton for a nutrient solution with 100 ppm Sr). This amount can be minimized by using Sr-specific resin to reduce the Sr concentration in the nutrient solution before adding the label.

Fractional Precipitation to Produce Unique Isotopic Fingerprints

The method creates isotopically labeled materials through partial crystallization.

As most Ca nitrate fertilizer is not used to grow *cannabis*, a company producing Ca nitrate fertilizer could divert a few percent of its material to the production of isotopically labeled nutrient solutions, and use the remainder as ordinary fertilizer, by:
1. Dissolving Ca nitrate in either water or (ideally) acetone.
2. Evaporating the solvent at or below room temperature until 95-99% of the dissolved material had precipitated.
3. Separating dissolved material from precipitate by filtration.
4. Returning the precipitated Ca nitrate to the ordinary fertilizer supply chain, while reserving the dissolved material for use as an isotopically labeled material.

Apart from Ca, fractional precipitation could be used to create isotopically labeled magnesium, potassium, and strontium. In the case of Sr, mass dependent isotope composition is separate and independent from the radiogenic enrichment in $^{87}$Sr discussed in the previous section, making it possible for Sr to function simultaneously as two isotopic labels.

By using Sr alone, or by combining radiogenic and mass dependent isotopic labels, it will be possible to impart a multi-dimensional isotopic fingerprint to *cannabis* products that would be nearly impossible to duplicate.

Supplementation of a Strontium Isotope Tracer in the Diet of Rhesus Macaques

Introduction

The following experiment used a Sr isotope tracer to detect bone loss in rhesus macaques. The methods used in these experiments are essentially the same as those described herein, and the results demonstrate the ability to introduce a unique isotopic fingerprint into a biological system (i.e., rhesus monkeys) via nutrient or dietary supplementation and to subsequently identify this fingerprint in biological samples.

Calcium homeostasis commonly is thought to involved the release of Ca from two distinct compartments: 1) a parathyroid hormone (PTH) mediated release of Ca from a relatively small labile non-mineralized pool or "bone compartment;" and 2) release of Ca from bone mineral via resorption by osteoclasts. The PTH mechanism can supply Ca on a timescale of minutes and is involved in maintaining short-term Ca homeostasis. By contrast, initiation of bone dissolution by osteoclasts is thought to require a week or more, and to be involved in long term Ca regulation.

Evidence for this two-compartment model of Ca homeostasis is indirect, and comes from isotopic tracer studies which reveal that Ca can be mobilized quickly in response to acute demand, interpreted in light of the fact that the intercellular communication needed to produce new populations of osteoclasts cannot occur on short timescales. If release of Ca from bone requires new populations of osteoclasts, it follows that some compartment other than bone must be the source of rapidly mobilized Ca.

However, the possibility remains that bone mineral can be mobilized by some mechanism other than the proliferation of osteoclasts. Determining the source of Ca available for rapid release has been difficult because there have been no techniques that readily detect bone resorption on short timescales. Bone loss can be inferred from elevated levels of resorption markers such as n-telepeptide (NTX), but the residence time of these markers in blood is long relative to the timescale on which rapid release of Ca must be studied, which limits the temporal resolution of changes in bone resorption. Moreover, resorption markers alone cannot distinguish between net bone mineral loss and an increase in bone remodeling rate that would produce no net movement of Ca from bone into blood. In spite of these problems, the assumption that bone Ca cannot be rapidly mobilized is challenged by observations of elevated NTX appearing within 24 hours of the initiation of bed rest, a well-known trigger of bone loss (Baecker et al, 2003).

Here evidence is presented that stress, another well studied cause of bone loss, can initiate bone resorption in rhesus monkeys within 24 hours, suggesting that bone itself can liberate Ca in response to acute demand. This evidence comes from two novel and complementary markers of bone mineral balance that employ Ca and Sr of natural isotopic composition, which track changes in bone mineral balance over timescales of a day or less. The Ca isotope system also permits Ca originating in mineral to be distinguished from Ca originating in other compartments.

Experimental

The experiment was not designed to measure the effect of stress, but observe the Ca isotopic signal associated with hypoestrogen (i.e., low levels of estrogen), a well-known cause of bone loss (see Results and Discussion). Six female rhesus monkeys, all between 11 and 14 years of age, were selected for an experimental investigation of the ability of natural Ca isotopes to track changes in bone mineral balance. All monkeys are housed in the UW Madison National Primate Center. All experimental procedures were reviewed and approved by an animal use board.

On the first day of the study, day −14, all monkeys were switched from their normal diet to a diet identical to their normal diet except that the $^{87}$Sr/$^{86}$Sr of the strontium naturally present had been altered (see Results and Discussion below and Materials and Methods). On day 0 or 1, all six monkeys were anesthetized for bone mineral density (BMD) and dual-energy x-ray absorptiometry (DEXA) measurements and were given injections of either DEPO-PRO-VERA® (medroxyprogesterone acetate) to suppress estrogen production (three monkeys) or saline (three monkeys). Urine samples were collected on days −14, −7, −2, −1, 0, 1, 2, 4, 6, 7, 8, 14, and 24. Blood samples (1 ml/sample by venous puncture) were collected on days −14, −1, 0, 8, 14 and 24. A single hair sample was collected from each animal approximately one month after the end of the study. Aliquots of all samples were chemically purified and analyzed for mass dependent Ca isotope fractionation (expressed as difference in the $^{44}$Ca/$^{42}$Ca ratio of the sample and a standard reference material) and for $^{87}$Sr/$^{86}$Sr.

Calcium Isotopes

The Ca isotope method employed differs from Ca isotope tracer studies in that relies on systematic changes in the relative abundance of the six naturally occurring Ca isotopes (40, 42, 43, 44, 46, and 48) caused by the changes in bone mineral balance. The relationship between Ca isotopes and bone mineral balance exists because bone mineral selectively incorporates lighter Ca isotopes, resulting in bone being enriched, and soft tissue being depleted, in light Ca isotopes. In contrast, bone loss releases isotopically light Ca into soft tissue. Discrimination against isotopically heavy Ca, or "fractionation," during bone formation is strictly mass-dependent, so that resulting changes in Ca isotope composition can be expressed as a change in the ratio of any two Ca isotopes (here $^{44}$C/$^{42}$Ca). Relative to a steady state of zero net bone growth, bone loss results in a drop in soft tissue $^{44}$C/$^{42}$Ca while bone growth increases this ratio in soft tissues. Details of the Ca isotope system are given elsewhere (Skulan et al, 2007, Skulan and DePaolo, 2000).

Strontium Isotopes

Sr is chemically similar to Ca and has similar behavior in the body. Like Ca, the large majority of Sr is in skeletal mineral where it can substitute for Ca in the apatite crystal lattice of bone.

Sr has four natural isotopes, with masses 84, 86, 87, and 88. Like Ca, Sr isotopes are subject to mass dependent fractionation. However $^{87}$Sr also is the daughter product of $^{87}$Rb, so that the ratio of $^{87}$Sr to other Sr isotopes (by convention expressed as $^{87}$Sr/$^{86}$Sr) in rocks is related to the Rb/Sr ratio of the rock and to its age.

Because measurements of $^{87}$Sr/$^{86}$Sr correct for mass-dependent Sr isotope fractionation, measured $^{87}$Sr/$^{86}$Sr is not affected by biological activity, but remains unchanged as Sr passes from bedrock to soil to plants and through subsequent trophic levels. Bulk skeletal $^{87}$Sr/$^{86}$Sr records the long-term average $^{87}$Sr/$^{86}$Sr of an animal's diet. Given the multi-year residence time of Sr in skeletal mineral, skeletal $^{87}$Sr/$^{86}$Sr can only change slowly in response to changes in dietary $^{87}$Sr/$^{86}$Sr, and is approximately constant over timescales of less than a few months.

In our Sr isotope technique a very small amount of Sr extracted from ancient granite was added to a $CaCO_3$ dietary supplement, raising its $^{87}$Sr/$^{86}$Sr from 0.70815 to 0.72100, while increasing the Sr concentration by a only 5%. The Sr was extracted from the ancient granite using the methods described herein except that hydrofluoric acid (HF) was used for the small scale extraction because it increased Sr yield.

This $CaCO_3$ dietary supplement was used to manufacture a batch of standard monkey chow with a uniform $^{87}$Sr/$^{86}$Sr of 0.71950, which was the sole food of the monkeys during the experiment. Monkeys were maintained on the new diet for two weeks, after which the only reservoir of "old" low $^{87}$Sr/$^{86}$Sr in their bodies was their skeleton. $^{87}$Sr/$^{86}$Sr subsequently measured in blood and urine reflects the relative contribution of bone and dietary Sr, and by proxy Ca, to total soft tissue Sr and Ca.

Results and Discussion

Figure 2:
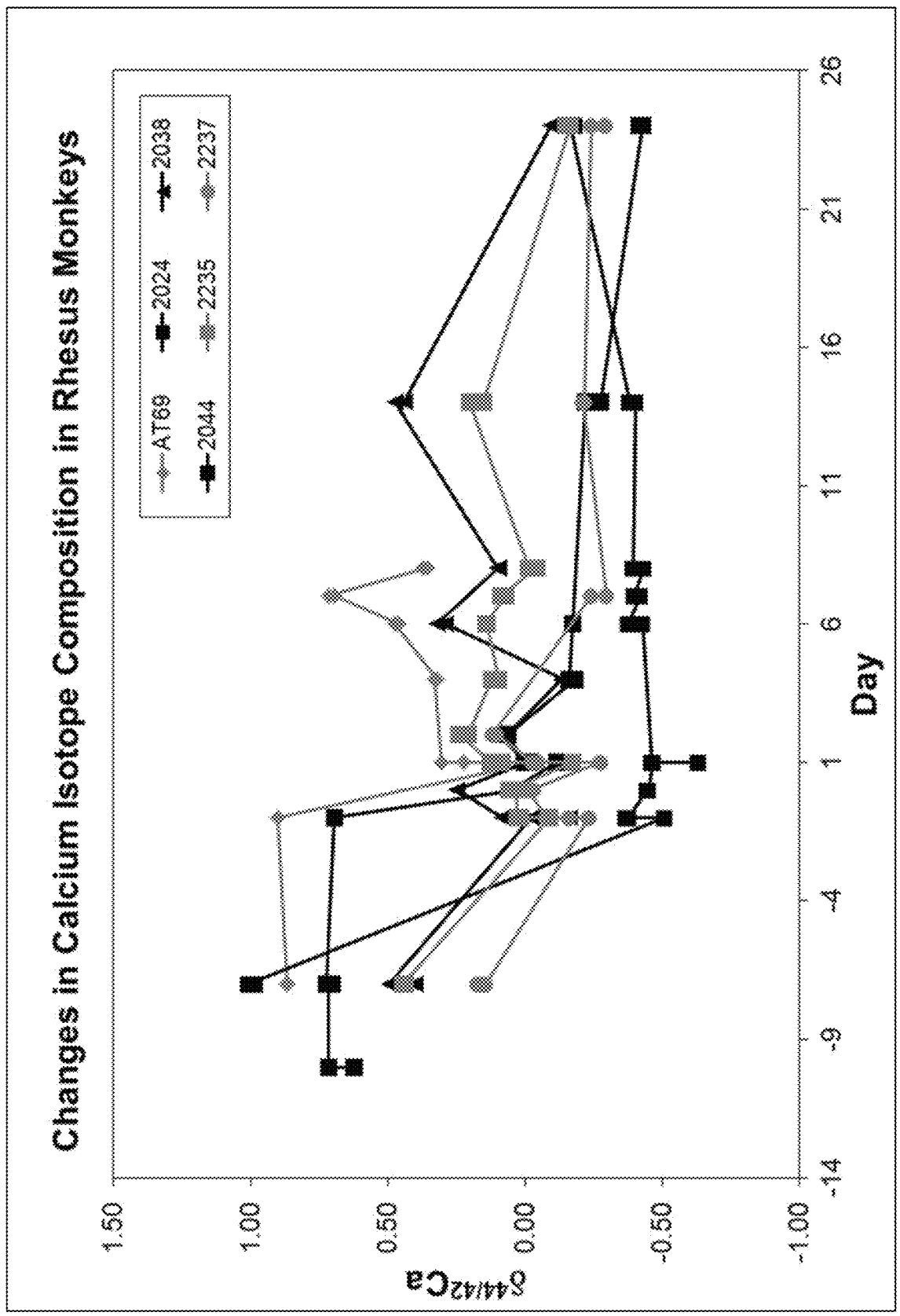
FIG. 2 depicts changes in calcium isotope composition in rhesus monkeys before and after experimentally induced bone loss.

Measurement of strontium isotope composition and calcium isotope composition in the six female rhesus monkeys is presented in FIG. 1 and FIG. 2. The $^{87}$Sr/$^{86}$Sr of the standard rhesus diet was between 0.70816 and 0.70945 (for calcium phosphate and calcium carbonate, respectively, which served as the dietary Ca source). The Sr extracted from the ancient granite had an 87/86 ratio of about 0.76500. This was added to the dietary calcium carbonate, which raised its 87/86 ratio to 0.71596. FIG. 1 shows that experimental samples ranged between about 0.708 and 0.7155, or between the old and new dietary values.

The most striking feature of the data is that, contrary to expectation, treatment and control groups both show a dramatic decrease in $^{87}$Sr/$^{86}$Sr on days 0 and 1, and in $^{44}$Ca/$^{42}$Ca on days −1 and 0. A drop in $^{87}$Sr/$^{86}$Sr alone could be interpreted as release of Sr (and Ca) from a non-mineralized Ca compartment, but this possibility is excluded by the nearly simultaneous drop in $^{44}$Ca/$^{42}$Ca, which indicates that fractionated bone mineral was the source of the Ca. Taken together these results show a sharp rise in net bone mineral loss starting on day −1, of a magnitude great enough to swamp any difference between the treatment and control groups.

All monkeys were anesthetized for BMD, DEXA, and injection. Anesthesia triggers cortisol secretion, and elevated cortisol is a well-known cause of bone loss. Urinary cortisol levels indeed were elevated in all monkeys when $^{87}$Sr/$^{86}$Sr and $^{44}$Ca/$^{42}$Ca dropped, but the drop in $^{44}$Ca/$^{42}$Ca began at least one day before monkeys were anesthetized, showing that the rise in cortisol could not be a direct response to anesthesia. However, on day −1 all of the monkeys housed with the experimental animals were anesthetized for routine biannual TB testing. Although anesthesia and TB testing was delayed for 1-2 days in the experimental monkeys, these animals were exposed to witnessing other members of their social group undergo a stressful procedure which they themselves had undergone dozens of times in the past. The experimental monkeys were not losing bone in direct response to anesthesia, but as a result of stress in anticipation of anesthesia.

Ca and Sr isotopes show the same general pattern, but differ in several respects. $^{44}$Ca/$^{42}$Ca begins to drop 1-2 days before $^{87}$Sr/$^{86}$Sr. This probably reflects the longer clearance time of Sr than Ca in soft tissues. A more substantial difference is that while $^{87}$Sr/$^{86}$Sr returned to pre-stress values after about 10 days, $^{44}$Ca/$^{42}$Ca remained depressed for the duration of the experiment (compare FIG. 1 and FIG. 2). Assuming that all of the pre-experimental Sr had been flushed from soft tissues by day 0 this difference in behavior may indicate the existence of a rapidly exchangeable Ca compartment in bone mineral. Such a compartment would quickly acquire the new dietary $^{87}$Sr/$^{86}$Sr but would release low $^{44}$Ca/$^{42}$Ca into soft tissue. Even if net bone mineral balance is negative, as is required in order to account for the sustained drop in $^{44}$Ca/$^{42}$Ca, the bulk of the Ca and Sr being released to soft tissue could be derived from a small, rapidly exchanging compartment.

CONCLUSION

Rhesus monkeys began to lose bone mineral within one day of being exposed to a stressful event, probably via a cortisol spike induced by the anticipation of anesthesia, demonstrating that bone mineral itself can be accessed quickly in response to Ca demand. These results do not refute the existence of a rapidly exchangeable "bone Ca compartment." Indeed the rapid recovery of $^{87}$Sr/$^{86}$Sr to pre-stress levels suggests the existence of such a compartment. However, the results do show that Ca in this compartment is stored in a mineralized form. These conclusions are made possible by novel biomarkers employing natural Ca and Sr isotopes, which make it possible to pinpoint the onset of bone loss with unprecedented temporal resolution.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

We claim:

1. A composition for tracing the source of a high value crop selected from the group consisting of *cannabis, ginseng*, a gourmet mushroom, a gourmet garlic, and a rare herb comprising:

a first element selected from the group consisting of strontium (Sr), neodymium (Nd), calcium (Ca), magnesium (Mg), potassium (K), boron (B), chlorine (Cl), copper (Cu), iron (Fe), manganese (Mn), molybdenum (Mo), zinc (Zn), and combinations thereof; and a second element comprising nitrogen (N), phosphorus (P), and potassium (K) in an amount sufficient to support the growth of a high value crop selected from the group consisting of *cannabis, ginseng*, a gourmet mushroom, a gourmet garlic, and a rare herb; and a third element comprising stable isotopes wherein stable isotopes of the third element are present in a mixture that provides an isotopic fingerprint for tracing the source of the high value crop into which the composition has been incorporated;

the mixture of stable isotopes is selected from the group consisting of $^{87}Sr/^{86}Sr$, $^{87}Sr/^{84}Sr$, $^{87}Sr/^{88}Sr$, $^{143}Nd/^{144}Nd$, $^{143}Nd/^{142}Nd$, $^{143}Nd/^{145}Nd$, $^{143}Nd/^{146}Nd$, $^{143}Nd/^{148}Nd$, $^{143}Nd/^{150}Nd$, $^{42}Ca/^{44}Ca$, $^{24}Mg/^{26}Mg$, $^{25}Mg/^{26}Mg$, $^{39}K/^{41}K$, $^{11}B/^{10}B$, $^{37}Cl/^{35}Cl$, $^{65}Cu/^{63}Cu$, $^{56}Fe/^{57}Fe$, $^{56}Fe/^{58}Fe$, $^{57}Fe/^{58}Fe$, $^{55}Mn/^{53}Mn$, $^{94}Mo/^{95}Mo$, $^{94}Mo/^{96}Mo$, $^{94}Mo/^{97}Mo$, $^{95}Mo/^{96}Mo$, $^{95}Mo/^{97}Mo$, $^{96}Mo/^{97}Mo$, $^{66}Zn/^{67}Zn$, $^{66}Zn/^{68}Zn$, $^{67}Zn/^{68}Zn$, and combinations thereof;

wherein the composition is incorporated into the high value crop during the growth of the high value crop.

2. The composition of claim 1, wherein the nitrogen (N) is present as a nitrate salt and/or the phosphorus (P) is present as a phosphate salt.

3. The composition of claim 1, wherein the composition is a hydroponic or aeroponic solution.

4. The composition of claim 1, wherein the concentration of the element is at least 10 ppm.

5. The composition of claim 1, wherein the composition comprises strontium (Sr) in a ratio of $^{87}Sr/^{86}Sr$ of greater than 1.0.

6. The composition of claim 1, wherein the composition comprises neodymium (Nd) in a ratio of $^{143}Na/^{144}Nd$ of greater than 0.5130 or less than 0.5100.

7. The composition of claim 1, wherein the composition is formulated as an aqueous solution or a seed treatment.

8. The composition of claim 1, further comprising an agriculturally acceptable carrier.

9. The composition of claim 8, wherein the agriculturally acceptable carrier is a dispersant, a surfactant, an additive, a thickener, an anticaking agent, a composting formulation, a granular application, diatomaceous earth, an oil, a coloring agent, a stabilizer, a preservative, or a polymer.

* * * * *